United States Patent [19]

Horrobin et al.

[11] 4,386,072

[45] May 31, 1983

[54] TREATMENT OF DISORDERS OF INFLAMMATION AND IMMUNITY AND DISORDERS ASSOCIATED WITH SMOOTH MUSCLE SPASM AND COMPOSITIONS THEREFOR

[76] Inventors: David F. Horrobin, P.O. Box 10, Nuns' Island, Montreal, Canada, H3E 1J8; Julian Lieb, 41 Village La., Bethany, Conn. 06525

[21] Appl. No.: 345,214

[22] Filed: Feb. 3, 1982

Related U.S. Application Data

[63] Continuation-in-part of Ser. No. 277,671, Jun. 26, 1981, abandoned.

[51] Int. Cl.³ .................... A61K 33/00; A61K 33/12; A61K 31/20
[52] U.S. Cl. .................................. 424/127; 424/153; 424/318
[58] Field of Search .................... 424/127, 153, 318

[56] References Cited

U.S. PATENT DOCUMENTS 3,993,775 11/1976 Williams .............................. 424/312

OTHER PUBLICATIONS

Johnson et al.–Lithium in Medical Practice (1978) pp. 29 & 30.
Harrobin–Chem. Abst. vol. 92 (1980), p. 82445k.
Delbarre et al.–Chem. Abst. vol. 94 (1981) p. 76954a.
Chem. Abst.–9th Collect Index (1972–1976) p. 40266cs.

*Primary Examiner*—Sam Rosen
*Attorney, Agent, or Firm*—Schwartz, Jeffery, Schwaab, Mack, Blumenthal & Koch

[57] ABSTRACT

A method for the treatment or prophylaxis of disorders of inflammation and immunity and disorders associated with smooth muscle spasm, by administering dihomo-γ-linolenic acid or a bioprecursor thereof conjointly with a physiologically acceptable lithium salt. Vitamin E and related tocopherols may optionally be also administered.

4 Claims, No Drawings

TREATMENT OF DISORDERS OF INFLAMMATION AND IMMUNITY AND DISORDERS ASSOCIATED WITH SMOOTH MUSCLE SPASM AND COMPOSITIONS THEREFOR

This application is a continuation-in-part of our pending application Ser. No. 277,671 filed June 26, 1981, now abandoned.

This invention relates to the treatment of disorders of inflammation and immunity as well as disorders associated with smooth muscle spasm.

Defects in the biosynthesis and/or metabolism of prostaglandins are now believed to play an important part in disorders of inflammation and immunity, and those associated with smooth muscle spasm.

For example, it has been found that the synovial tissues from patients suffering from rheumatoid arthritis produce larger amounts of prostaglandin E2 (PGE2) and prostaglandin F2α (PGF2α) compared to the synovial tissues from unaffected subjects.

Prostaglandin E1 (PGE1) is a compound which has been found to be of importance in the maintenance of the normal body metabolism, and this compound is synthesised in the body from its bioprecursor, dihomo-γ-linolenic acid (DGLA). In order therefore to ensure that physiologically acceptable amounts of PGE1 are maintained in the body, it is necessary to provide sufficient DGLA and make sure that the conversion of DGLA to PGE1 proceeds normally. DGLA is itself biosynthesised from the precursor substance, γ-linolenic acid, and this latter substance is in turn biosynthesised from linoleic acid.

It has been proposed that multiple sclerosis is associated with an imbalance in the normal levels of the prostaglandins, PGE1 and PGE2. The latter substance is biosynthesised in the body from arachidonic acid.

The administration of lithium, and in particular lithium salts such as lithium carbonate, has found widespread application in the treatment of manic-depressive psychosis. Lithium treatment has been reported as being particularly effective in the treatment of the manic phase of this illness and also in the prophylaxis of both manic and depressive relapses. We have found that lithium can inhibit or block the conversion of DGLA stored in the body to PGE1.

U.S. Pat. No. 3,639,625 (issued Feb. 1, 1972 to Sherwin) describes therapeutic compositions containing lithium succinate for treating dermatitis and for producing an antipruritic effect, the compositions thus being suitable for topical application.

It is an object of the invention to alleviate disorders of inflammation and immunity as well as disorders associated with smooth muscle spasm, which are the result of the defective biosynthesis and/or metabolism of prostaglandin E1.

Thus, in one aspect the invention provides a method for the treatment and/or prophylaxis of disorders of inflammation and immunity and disorders associated with smooth muscle spasm in a subject, which disorders are characterised by defective biosynthesis and/or metabolism of prostaglandin E1, which method comprises administering to the subject an effective amount therefor of dihomo-γ-linolenic acid or a biosynthetic precursor thereof conjointly with a physiologically acceptable lithium salt.

Whilst not wishing to be bound by theory, it is believed that disorders of immunity and inflammation as well as disorders associated with smooth muscle spasm are the result of inadequate regulation of the formation of PGE1 in the body. Thus, PGE1 is essential for the normal functioning of the immune system and is involved in controlling inflammatory disorders with the result that both PGE1 levels which are too high or too low may be harmful. In addition, PGE1 regulates the functioning of smooth muscle in a variety of tissues of the body, including blood vessels, again with the result that either too much or too little PGE1 may be harmful.

It is now believed that the above mentioned disorders may be related to excessive conversion of dihomo-γ-linolenic acid to PGE1, which leads to a depletion of the body's stores of DGLA and hence to a deficiency of DGLA and thus of PGE1. This results in levels of PGE1 in the body which fluctuate in an uncontrolled manner, being too high when the body's DGLA stores are high and being too low when the stores are depleted, and may therefor explain the cyclical nature of many of the above disorders. The situation may be likened to an irrigation tank with no tap or valve on the outflow pipe. When it rains and the tank is full, there is a massive uncontrolled outflow of water which rapidly leads to emptying of the tank and drying up of the water supply as soon as the rain stops. In order to provide a smooth steady supply of water it is necessary to both fill up the tank and control the outflow. Therefore in the method of the invention a smooth steady biosynthesis and metabolism of PGE1 is provided by administering dihomo-γ-linolenic acid or a bioprecursor thereof such as γ-linolenic acid or linoleic acid, together with a physiologically acceptable lithium salt to control the biosynthesis of PGE1 from its precursors.

Concomitant with the production of prostaglandins in the body from dihomo-γ-linolenic acid, other bioproducts are formed from this acid as a result of the action of the enzyme, lipoxygenase. These lipoxygenase products exhibit an inflammatory action. We have found that the formation of the lipoxygenase products may be inhibited or blocked in the presence of vitamin E and related tocopherols. Thus, in a preferred embodiment of the invention, a tocopherol which is capable of inhibiting the formation of lipoxygenase products, e.g. vitamin E and/or related tocopherols, or any other physiologically acceptable lipoxygenase inhibitor, is conjointly administered.

Disorders of inflammation and immunity which may be treated by the method according to the invention are those disorders characterised by defective PGE1 biosynthesis and metabolism. Such disorders include, for example, rheumatoid and allergic arthritis, multiple sclerosis, lymphadenopathy, idiopathic thrombocytopenic purpura, ankylosing spondylitis, psoriasis, eczema, Crohn's Disease, ulcerative colitis and related diseases. Similarly, disorders associated with smooth muscle spasm may be treated according to the invention, and such disorders include asthma, migraine, Raynaud's Syndrome, disorders of gastrointestinal motility and conditions arising from coronary spasm such as angina pectoris and myocardial infarction.

In the method of treatment according to the invention, the DGLA may be replaced by an equivalent amount of a biosynthetic precursor thereof such as the above-mentioned γ-linolenic acid or linoleic acid. If desired, these substances may be administered in admixture. These substances may also be administered in the form of physiologically acceptable functional derivatives thereof such as, for example, their $C_1-C_4$ alkyl (e.g. methyl and ethyl) esters and the triglycerides of the acids. Convenient sources of linoleic acid for administration in the methods according to the invention are the many vegetable oils of which it forms a major constituent. Examples of such oils include cotton seed, soyabean, peanut, corn, sunflower seed, safflower, poppy seed, linseed and perilla oils, where the linoleic acid occurs in the form of its triglyceride. In the method of the invention, these vegetable oils may be administered as such i.e. without any treatment to isolate the linoleic acid therefrom. When such oils are used in the method of the invention, they may conveniently be administered in an amount of from 0.5 to 100 g per day in suitably divided doses.

At the present time known sources of oils having a high γ-linolenic acid content are few. One source currently available is the seed of the Evening Primrose or *Oenothera biennis L*, the oil extract therefrom containing γ-linolenic acid and linoleic acid in the form of their triglycerides. Another source of γ-linolenic acid is the seed of *Borago officinalis* which provides a richer source of γ-linolenic acid with smaller amounts of linoleic acid. Again, these seed oil extracts may be used as such or may, if desired, be fractionated to yield an oil composition enriched in the desired γ-linolenic and/or linoleic acids.

Dihomo-γ-linolenic acid for administration according to the invention may be prepared from γ-linolenic acid according to known methods.

Convenient daily doses of dihomo-γ-linolenic acid or γ-linolenic acid in the methods according to the invention are, for example, from 50 mg to 100 g per day, suitably in divided doses.

Lithium is administered according to the invention in the form of a physiologically acceptable salt such as, for example, lithium carbonate, although other physiologically acceptable lithium salts may be employed. Lithium carbonate is generally administered orally in a low initial dose of 20 mg, but this may be as high as 250 or 300 mg daily, which may if desired be gradually increased to 750 mg daily in divided doses. In severely affected subjects up to 2.0 g per day may be administered. The lithium plasma level is generally monitored, e.g. once or twice weakly, during the course of treatment and the rate of administration adjusted to produce a suitable concentration in the plasma, e.g. of 0.3 to 1.6 mM lithium per liter. If convenient, it may be appropriate to administer the lithium in the form of a salt with the above mentioned acids, that is with dibromo-γ-linolenic, γ-linolenic or linoleic acid. In which case, it may not be necessary to separately administer the acids per se.

The invention also includes within its scope pharmaceutical compositions adapted for oral administration which comprise at least one compound selected from the group consisting of dihomo-γ-linolenic acid, γ-linolenic acid and linoleic acid, together with at least one physiologically acceptable lithium salt. The compositions preferably additionally contain a tocopherol which is capable of inhibiting the formation of lipoxygenase products such as, for example, vitamin E and/or related tocopherols.

We claim:

1. A method for the treatment and/or prophylaxis of disorders of inflammation and immunity and disorders associated with smooth muscle spasm in a subject, which method comprises administering to the subject an effective amount therefor of dihomo-γ-linolenic acid, γ-linolenic acid or linoleic acid conjointly with a physiologically acceptable lithium salt.

2. A method according to claim 1 wherein at least one compound selected from the group consisting of vitamin E and related tocopherols is additionally administered.

3. A pharmaceutical composition adapted for oral administration which comprises effective amounts of at least one compound selected from the group consisting of dihomo-γ-linolenic acid, γ-linolenic acid and linoleic acid, together with effective amounts of at least one physiologically acceptable lithium salt.

4. A composition according to claim 3 additionally containing effective amounts of at least one compound selected from the group consisting of vitamin E and related tocopherols.

* * * * *